US008647888B2

(12) United States Patent
Baydoun

(10) Patent No.: US 8,647,888 B2
(45) Date of Patent: Feb. 11, 2014

(54) IMMUNOASSAY TEST STRIP FOR USE IN A DIAGNOSTIC SYSTEM

(75) Inventor: Lina Baydoun, Gilroy, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 13/250,028

(22) Filed: Sep. 30, 2011

(65) Prior Publication Data

US 2012/0082598 A1 Apr. 5, 2012

Related U.S. Application Data

(60) Provisional application No. 61/389,171, filed on Oct. 1, 2010.

(51) Int. Cl.
*G01N 33/563* (2006.01)
*G01N 33/558* (2006.01)
*G01N 33/544* (2006.01)

(52) U.S. Cl.
USPC ............................ 436/513; 436/514; 436/528

(58) Field of Classification Search
USPC .......................................... 436/514, 528–530
See application file for complete search history.

(56) References Cited

U.S. PATENT DOCUMENTS

| 5,079,171 | A | 1/1992 | Senyei et al. |
| 5,096,830 | A | 3/1992 | Senyei et al. |
| 5,185,270 | A | 2/1993 | Senyei et al. |
| 5,223,440 | A | 6/1993 | Teng et al. |
| 5,236,846 | A | 8/1993 | Senyei et al. |
| 5,281,522 | A | 1/1994 | Senyei et al. |
| 5,468,619 | A | 11/1995 | Senyei et al. |
| 5,516,702 | A | 5/1996 | Senyei et al. |
| 5,607,863 | A * | 3/1997 | Chandler ...................... 436/518 |
| 5,686,315 | A | 11/1997 | Pronovost et al. |
| 6,087,184 | A * | 7/2000 | Magginetti et al. ........... 436/514 |
| 6,267,722 | B1 | 7/2001 | Anderson et al. |
| 6,375,896 | B1 * | 4/2002 | Wuske et al. ................. 422/411 |

(Continued)

FOREIGN PATENT DOCUMENTS

| EP | 1936376 A2 | 6/2008 |
| WO | 2006026020 A2 | 3/2006 |
| WO | 2006119160 A2 | 11/2006 |

OTHER PUBLICATIONS

International Search Report mailed Dec. 15, 2011, in related International Application No. PCT/US2011/054236, filed Sep. 30, 2011.

(Continued)

*Primary Examiner* — Shafiqul Haq
*Assistant Examiner* — Gary E Hollinden
(74) *Attorney, Agent, or Firm* — Vista IP Law Group LLP

(57) ABSTRACT

An immunoassay test strip includes a sample pad for receiving a liquid patient sample; a conjugate pad fluidly coupled to the sample pad, wherein the conjugate pad contains a substantially uniform application of conjugate reagent; a contact pad fluidly coupled to the conjugate pad; a porous or bibulous member, e.g., made from nitrocellulose, fluidly coupled to the contact pad which is capable or transporting a liquid sample along the test strip, wherein the porous or bibulous member serves as the solid support upon which immunoreactions occur, and an absorbent pad fluidly coupled to the porous or bibulous member, which serves to draw sample fluid introduced onto the sample pad through the respective conjugate pad, contact pad and porous or bibulous member.

8 Claims, 6 Drawing Sheets

(56) References Cited

U.S. PATENT DOCUMENTS

| | | | |
|---|---|---|---|
| 6,394,952 B1 | 5/2002 | Anderson et al. | |
| 6,399,398 B1* | 6/2002 | Cunningham et al. | 436/534 |
| 6,699,722 B2* | 3/2004 | Bauer et al. | 436/518 |
| 6,867,051 B1 | 3/2005 | Anderson et al. | |
| 8,377,710 B2* | 2/2013 | Whitesides et al. | 436/169 |
| 2003/0013206 A1* | 1/2003 | Takahashi et al. | 436/514 |
| 2003/0219908 A1* | 11/2003 | Davis et al. | 436/514 |
| 2004/0023412 A1* | 2/2004 | Carlsson et al. | 436/514 |
| 2004/0082077 A1* | 4/2004 | Hu | 436/514 |
| 2004/0137640 A1* | 7/2004 | Hirao et al. | 436/514 |
| 2004/0266025 A1* | 12/2004 | Hickok et al. | 436/518 |
| 2006/0003390 A1* | 1/2006 | Schaffler et al. | 435/7.9 |
| 2006/0018800 A1 | 1/2006 | Slowey et al. | |
| 2006/0024722 A1* | 2/2006 | Fischer-Colbrie et al. | 435/6 |
| 2006/0068501 A1* | 3/2006 | Li et al. | 436/514 |
| 2006/0160078 A1* | 7/2006 | Cardy et al. | 435/6 |
| 2006/0240541 A1 | 10/2006 | Petruno et al. | |
| 2011/0229913 A1* | 9/2011 | Bae et al. | 435/7.32 |

OTHER PUBLICATIONS

Written Opinion mailed Dec. 15, 2011, in related International Application No. PCT/US2011/054236, filed Sep. 30, 2011.

* cited by examiner

IMMUNOASSAY TEST STRIP FOR USE IN A DIAGNOSTIC SYSTEM

RELATED APPLICATION DATA

The present application claims the benefit under 35 U.S.C. §119 to U.S. Provisional Patent Application Ser. No. 61/389,171, filed on Oct. 1, 2010, which is hereby incorporated by reference into the present application in its entirety.

FIELD OF THE DISCLOSED INVENTIONS

The inventions disclosed in the present application pertain to systems and methods that aid in providing a medical diagnosis or risk assessment for a patient using biochemical and historic patient data, including data from point of care diagnostic tests or assays, and processing the information to give an indication of a medical condition or risk. In particular, the present application discloses and describes an improved immunoassay test strip for use in a diagnostic system and related methods, such as the diagnostic systems and methods disclosed and described in U.S. Pat. Nos. 6,267,722, 6,394,952 and 6,867,051, each of which is fully incorporated herein by reference.

BACKGROUND

The above-incorporated U.S. Pat. Nos. 6,267,722, 6,394,952 and 6,867,051 disclose and describe objective techniques that reduce the error associated with interpreting immuno-chromato-graphic and other assay test results, including providing systems, methods, devices and instruments for objectively assessing data from biochemical and other tests and to use such data for diagnosis and risk assessment, including the incorporation of decision-support methodologies into such systems and thereby enhance the diagnostic and risk assessment capabilities thereof.

More specifically, the above-incorporated U.S. Pat. Nos. 6,267,722, 6,394,952 and 6,867,051 disclose and describe systems and methods for detecting and measuring levels of a target analyte in a patient sample, analyzing the resulting data, and providing a diagnosis or risk assessment. The systems and methods include an assay device in combination with a reader, particularly a computer-assisted reader, such as a reflectance reader, and data processing software employing data reduction and curve fitting algorithms, optionally in combination with a trained neural network for accurately determining the presence or concentration of analyte in a biological sample. The methods include performing an immunoassay assay on a patient sample using a specially constructed test strip, reading the data using a reflectance reader, and processing the reflectance data using data processing software employing data reduction algorithms. Software, including curve fitting algorithms, optionally in combination with a trained neural network, is used to determine the presence or amount of analyte in a given sample. The data obtained from the reader then can be further processed by the medical diagnosis system to provide a risk assessment or diagnosis of a medical condition as output.

In an exemplary embodiment, the assay device is a lateral flow test strip encased in a housing designed to be read by the reader, and the assay is a sandwich immunoassay. A patient sample is contacted with an antibody for a selected target analyte indicative of a disease, disorder or risk thereof. The antibody is labeled by conjugation to a physically detectable label, and upon contact with the sample containing the target analyte forms a complex, wherein the antibody-analyte complex is then contacted with a second antibody for the antigen, which is immobilized on a solid support. The second antibody captures the antibody-analyte complex to form an antibody-analyte-antibody sandwich complex, and the resulting complex, which is immobilized on the solid support, is detected by virtue of the label. The test strip is then inserted into a reader, where the signal from the label in the complex is measured. Additionally, the test strip may be enclosed within a housing that includes an identifying symbol, such as a bar code, which is also read by the reader and contains data related to the assay device and/or test run.

The signal obtained is processed using data processing software employing data reduction and curve fitting algorithms, optionally in combination with a trained neural network, to give either a qualitative (i.e., a positive or negative) result, or a quantitative determination of the concentration of analyte in the sample, which is correlated with a result indicative of a risk or presence of a disease or disorder. The result can optionally be input into a decision support system, and processed to provide an enhanced assessment of the risk of a medical condition as output. The entire procedure may be automated and/or computer-controlled.

The analyte to be detected may be fetal fibronectin (fFN) and the result obtained is a positive or negative indication of pregnancy or the risk of certain pregnancy-related conditions or fertility and infertility-related conditions, including ectopic pregnancy, preterm labor, pre-eclampsia, imminent delivery, term induction and fetal membrane rupture. Thus, the above-incorporated U.S. Pat. Nos. 6,267,722, 6,394,952 and 6,867,051 disclose and describe a rapid fFN test using a lateral flow test device, which provides a means to detect and to quantitate concentrations of fFN throughout pregnancy and to assess the risk and detect conditions associated therewith. Because of the sensitivity of the combination of the reader and devices provided herein, fFN may be monitored throughout pregnancy, including times when it is not detected by less sensitive systems.

Point of Care Diagnostic and Risk Assessment Systems

The above-incorporated U.S. Pat. Nos. 6,267,722, 6,394,952 and 6,867,051 disclose and describe systems for diagnosing and assessing certain medical risks. The systems are designed for use on site at the point of care, where patients are examined and tested, as well as for operation remote from the site. The systems are designed to accept input in the form of patient data, including, but not limited to biochemical test data, physical test data, historical data and other such data, and to process and output information, such as data relating to a medical diagnosis or a disease risk indicator. The patient data may be contained within the system, such as medical records or history, or may be input as a signal or image from a medical test or procedure, for example, immunoassay test data, blood pressure reading, ultrasound, X-ray or MRI, or introduced in any other form. Specific test data can be digitized, processed and input into the medical diagnosis expert system, where it may be integrated with other patient information. The output from the system is a disease risk index or medical diagnosis.

Point of care testing refers to real time diagnostic testing that can be done in a rapid time frame so that the resulting test is performed faster than comparable tests that do not employ this system. For example, the exemplified fFN immunoassay disclosed and described in the above-incorporated U.S. Pat. Nos. 6,267,722, 6,394,952 and 6,867,051 is performed in significantly less time than the fFN ELISA assay, e.g., in less than half an hour. In addition, point of care testing refers to testing that can be performed rapidly and on site, such as in a doctor's office, at a bedside, in a stat laboratory, emergency room or other such locales, particularly where rapid and accurate results are required. In general, "diagnosis" refers to a predictive process in which the presence, absence, severity or course of treatment of a disease, disorder or other medical condition is assessed. For purposes herein, diagnosis will also include predictive processes for determining the outcome resulting from a treatment. As used herein, risk refers to a predictive process in which the probability of a particular outcome is assessed.

In an exemplary embodiment, a point of care diagnostic and risk assessment system includes a reader, such as a reflectance or transmission reader, such as a reflectance reader, for reading patient data, a test device designed to be read in the reader, and software for analysis of the data. A test strip device in a plastic housing is designed for use with the reader, optionally including a symbology, such as an alphanumeric character bar code or other machine-readable code, and software designed for analysis of the data generated from the test strip are also provided.

Assays

The above-incorporated U.S. Pat. Nos. 6,267,722, 6,394,952 and 6,867,051 disclose and describe systems for performing assays, including but are not limited to: nucleic acid detection, including using amplification and non-amplification protocols, any assay that relies on calorimetric or spectrometric detection, including fluorometric, luminescent detection, such as creatine, hemoglobin, lipids, ionic assays, blood chemistry. Immunoassays, including competitive and non-competitive immunoassays, are among those preferred for determination of the presence or amount of analyte in a patient sample. An immunoassay may be any method using a preferential binding of an antigen with a second material, a binding partner, usually an antibody or another substance having an antigen binding site, which binds preferentially with an epitope of the fetal restricted antigen. Preferential binding, as used herein, refers to binding between binding partners that is selective and generally specific, and demonstrates less than 10%, preferably less than 5%, cross-reactive nonspecific binding. Such immunoassay methods include any known to those of skill in the art, including, but not limited to, sandwich, competition, agglutination or precipitation. Any known immunoassay procedure, particularly those that can be adapted for use in combination with lateral flow devices as described herein, can be used in the systems and methods provided in the above-incorporated U.S. Pat. Nos. 6,267,722, 6,394,952 and 6,867,051, and also further provided herein.

Test Device

Any device which is compatible for use with a reader, such as a reflectance reader, for determining the assay result is contemplated for use herein. As used herein, a "test strip" refers to any means on which patient test data or other data is generated, recorded or displayed in a manner that forms an image or from which an image can be generated. Such strips, include, but are not limited to, immunochromatographic test strips, such as lateral flow devices, X-ray films, such as X-rays and films produced from sequencing gels, EKG printouts, MRI results and other such means that generate or from which an image can be generated. The strip is may be adapted for scanning or reading by a reader. Although referred to as a "strip", a test strip can be of any shape or geometry, including rectangular, three dimensional, circular, and so forth. Test strips that may be adapted for use in combination with a reader are disclosed and described in the above-incorporated U.S. Pat. Nos. 6,267,722, 6,394,952 and 6,867,051.

Typically these test devices are intended for use with biological samples, such as saliva, blood, serum, cerebral spinal fluid, cervico-vaginal samples, for example. Other biological samples, such as food samples, which are tested for contamination, such as by bacteria or insects, are also contemplated. Target analytes include, but are not limited to: nucleic acids, proteins, peptides, such as human immunodeficiency virus (HIV) antigens, antigens indicative of bacterial, such as *Salmonella* and *E. coli*, yeast or parasitic infections, apolipoprotein(a) and lipoprotein(a), environmental antigens, human chorionic gonadotropin (hCG), E-3-G, interleukins and other cytokines and immunomodulatory proteins, such as IL-6 and interferon, small nuclear ribonuclear particles (snRNP) antigens, fFN and other indicators, such as IGF binding protein-1, of pregnancy related disorders.

Immunoassay Test Strip

An exemplary prior art immunoassay test strip disclosed and described in the above-incorporated U.S. Pat. Nos. 6,267,722, 6,394,952 and 6,867,051 includes a membrane system that defines a liquid flow pathway, as shown in FIGS. 1A and 1B, which are described below in detail. Such lateral flow test immunoassay devices are among those preferred for performing immunoassays, wherein a membrane system forms a single fluid flow pathway along the test strip. The membrane system includes components that act as a solid support for immunoreactions. For example, porous or bibulous or absorbent materials may be placed on a strip such that they partially overlap, or a single material can be used, in order to conduct liquid along the strip. The membrane materials may be supported on a backing, such as a plastic backing. In an exemplary prior art embodiment, the test strip includes a glass fiber pad, a nitrocellulose strip and an absorbent cellulose paper strip supported on a plastic backing Antibodies that react with the target analyte and/or a detectable label system are immobilized on the solid support. A "solid support" refers to the material to which the antibody is linked. A variety of materials can be used as the solid support. The support materials include any material that can act as a support for attachment of the molecules of interest. Such materials are known to those of skill in this art. These materials include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone, rayon, nylon, polyethylene, polypropylene, polybutylene, polycarbonate, polyesters, polyamides, vinyl polymers, polyvinylalcohols, polystyrene and polystyrene copolymers, polystyrene crosslinked with divinylbenzene or the like, acrylic resins, acrylates and acrylic acids, acrylamides, polyacrylamides, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, or other commercially available media.

The antibodies may be bound to the test strip by adsorption, ionic binding, van der Waals adsorption, electrostatic binding, or by covalent binding, by using a coupling agent, such as glutaraldehyde. In the prior art test strip shown in FIGS. 1A and 1B, the antibodies are applied to the conjugate pad and nitrocellulose strip using a volumetric ceramic piston pump dispenser to stripe antibodies that bind the analyte of interest, including a labeled antibody conjugate, onto the glass fiber conjugate pad and the nitrocellulose strip. The test strips may or may not be otherwise treated, for example, with sugar to facilitate mobility along the test strip or with water-soluble non-immune animal proteins, such as albumins, including bovine (BSA), other animal proteins, water-soluble polyamino acids, or casein to block non-specific binding sites.

An anti-fFN antibody is an antibody that binds selectively with fFN. Such antibodies are known to those of skill in the art and also may be readily isolated. Fetal restricted antigens refers to antigen that are present in pregnant women uniquely, or in substantially elevated amounts compared to non-pregnant women in maternal serum, plasma, urine, saliva, sweat, tears and other bodily fluids. Fetal fibronectin is a fetal restricted antigen found in placenta, amniotic fluid and fetal connective tissue, which differs structurally from adult fibronectins. Fetal fibronectin is not present in significant quantities in maternal plasma or serum, and may be captured with a general binding antibody, such as an anti-fibronectin antibody, or an anti-fetal restricted antigen antibody, such as anti-fetal fibronectin antibody.

Test Strip Housing

The test strip optionally may be contained within a customized housing shaped for insertion into the reflectance reader. The housing may be made of plastic or other inert material that does not interfere with the assay procedure. An exemplary prior art assay device, including a test strip and housing assembly disclosed and described in the above-incorporated U.S. Pat. Nos. 6,267,722, 6,394,952 and 6,867,051, FIGS. 2-5, which are described in detail below.

The test strip housing may include a symbology, such as a bar code that can be associated with data related to the assay device, patient data and/or test run. For example, information associated with the device, such as lot number, expiration date, analyte and intensity value, or information related to the test run, such as date, reflectance value or other such information, can be encoded and associated, such as in a database with a bar code imprinted on the device. FIGS. 2A, 2B and 3 depict assay devices that optionally include bar codes, 216 and 316, respectively.

Antibodies

Any antibody, including polyclonal or monoclonal antibodies, or any fragment thereof, such as the Fab fragment, that binds the analyte of interest, is contemplated for use with the test strips disclosed and described herein. Monoclonal and/or polyclonal antibodies may be used. For example, a mouse monoclonal anti-fetal fibronectin antibody may be used in a labeled antibody-conjugate for detecting fetal fibronectin, and a polyclonal goat anti-mouse antibody may also be used to bind fetal fibronectin to form a sandwich complex. An antibody that binds to the labeled antibody conjugate that is not complexed with fetal fibronectin may be immobilized on the test strip and used as a control antibody. For example, when fetal fibronectin is the analyte, a polyclonal goat anti-mouse IgG antibody may be used.

An antibody that will bind the analyte of interest is conjugated to a detectable label. In a particular embodiment, where fetal fibronectin is to be detected, a mouse monoclonal anti-fFN antibody (see, e.g., U.S. Pat. No. 5,281,522), conjugated to latex particles containing a blue dye may be used. In one embodiment, a goat polyclonal antibody to human fibronectin is conjugated to a colloidal gold label. In an exemplary embodiment, an antibody that binds the labeled antibody conjugate that is not complexed with fetal fibronectin is used as a control antibody. For example, where the labeled conjugate includes a monoclonal anti-fetal fibronectin antibody, a polyclonal goat anti-mouse IgG antibody is used. The antibodies may be raised and purified using methods known to those of skill in the art or obtained from publicly available sources.

Conjugation of the Antibody to a Label

An antibody conjugate containing a detectable label may be used to bind the analyte of interest. The detectable label used in the antibody conjugate may be any physical or chemical label capable of being detected on a solid support using a reader, such as a reflectance reader, and capable of being used to distinguish the reagents to be detected from other compounds and materials in the assay. Suitable antibody labels are well known to those of skill in the art. The labels include, but are not limited to enzyme-substrate combinations that produce color upon reaction, colored particles, such as latex particles, colloidal metal or metal or carbon sol labels, fluorescent labels, and liposome or polymer sacs, which are detected due to aggregation of the label. An exemplary label is a colored latex particle. Colloidal gold may also be used in the labeled antibody conjugate.

The label may be derivatized for linking antibodies, such as by attaching functional groups, such as carboxyl groups to the surface of a particle to permit covalent attachment of antibodies. Antibodies may be conjugated to the label using well known coupling methods. Coupling agents such as glutaraldehyde or carbodiimide may be used. The labels may be bonded or coupled to the antibodies by chemical or physical bonding. A carbodiimide coupling reagent, 1-ethyl-3-(3-dimethylaminopropyl)carbodiimide (EDAC), may be used to link antibodies to latex particles.

Measurement of Analytes

Any analyte that can be detected in any assay, particularly colorimetric assays, including immunoassays, and that can be associated with a disorder is contemplated for as a target. Suitable analytes are any which can be used, along with a specific binding partner, such as an antibody, or a competitor, such as an analog, in an assay. Analytes may include, but are not limited to proteins, haptens, immunoglobulins, enzymes, hormones (e.g., hCG, LH, E-3-G estrone-3-glucuronide and P-3-G (progestrone-3-glucuronide)), polynucleotides, steroids, lipoproteins, drugs, bacterial or viral antigens, such as *Streptococcus, Neisseria* and *Chlamydia*, lymphokines, cytokines, and the like. A number of suitable analytes are described in U.S. Pat. No. 5,686,315, which is fully incorporated herein by reference. Although examples are provided for the determination of fetal fibronectin in cervicovaginal samples, the systems and methods disclosed and described in the above-incorporated U.S. Pat. Nos. 6,267,722, 6,394,952 and 6,867,051, and further provided herein, are not limited to the detection and measurement of fetal fibronectin, but apply to any biochemical test, particularly those for which test strips can be developed or for which test strips are known.

Test Strip for Measuring fFN and Cellular Fibronectin

Methods for measuring fetal fibronectin and cellular fibronectin levels in cervicovaginal samples are known, (see, e.g., U.S. Pat. Nos. 5,096,830, 5,185,270, 5,223,440, 5,236, 846, 5,281,522, 5,468,619 and 5,516,702, which are fully incorporated by reference herein), and diagnostic tests for various pregnancy-related disorders are available (see, e.g., U.S. Pat. Nos. 5,096,830 and 5,079,171, which are also fully incorporated by reference herein). These methods can be adapted for use with the immunoassay test strips and devices described herein.

Fetal Fibronectin Assay Procedure

In conducting the assay, a patient sample is obtained. The sample may include fluid and particulate solids, and, thus, can be filtered prior to application to the assay test strip. The sample may be removed from the patient using a swab having a fibrous tip, an aspirator, suction or lavage device, syringe, or any other known method of removing a bodily sample, including passive methods for collecting urine or saliva. In particular, the sample may be extracted into a buffer solution, and optionally heated, for example, at 37° C., and filtered. Where fetal fibronectin is to be detected in a sample, the sample is obtained from in the vicinity of the posterior fornix, the ectocervix or external cervical os using a swab having a dacron or other fibrous tip.

A volume of the test sample is then delivered to the test strip using any known means for transporting a biological sample, for example, a standard plastic pipet. Any analyte in the sample binds to the labeled antibody and the resulting complex migrates along the test strip. Alternatively, the sample may be pre-mixed with the labeled conjugate prior to applying the mixture to the test strip. When the labeled antibody-analyte complex encounters a detection zone of the test strip, the immobilized antibody therein binds the complex to form a sandwich complex, thereby forming a colored stripe. Any unbound latex-conjugated antibody continues to migrate into a control zone where it is captured by a second immobilized antibody or other agent capable of binding the conjugate, and thereby forms a second colored stripe due to the aggregation of the dye-containing latex beads. This indicates that the assay run has completed.

Reader

A reader refers to an instrument for detecting and/or quantitating data, such as on test strips. The data may be visible to the naked eye, but does not need to be visible. Such readers are disclosed and described in the above-incorporated U.S. Pat. Nos. 6,267,722, 6,394,952 and 6,867,051. As disclosed and described therein, a reflectance reader refers to an instrument adapted to read a test strip using reflected light, including fluorescence, or electromagnetic radiation of any wavelength. Reflectance can be detected using a photodetector or other detector, such as charge coupled diodes (CCD). A exemplary reflectance reader includes a cassette slot adapted to receive a test-strip, light-emitting diodes, optical fibers, a sensing head, including means for positioning the sensing head along the test strip, a control circuit to read the photodetector output and control the on and off operation of the light-emitting diodes, a memory circuit for storing raw and/or processed data, and a photodetector, such as a silicon photodiode detector. It will be appreciated that a color change refers to a change in intensity or hue of color or may be the appearance of color where no color existed or the disappearance of color.

In an exemplified embodiment disclosed and described in the above-incorporated U.S. Pat. Nos. 6,267,722, 6,394,952 and 6,867,051, a sample is applied to a diagnostic immunoassay test strip, and colored or dark bands are produced. The intensity of the color reflected by the colored label in the test region (or detection zone) of the test strip is, for concentration ranges of interest, directly proportional or otherwise correlated with an amount of analyte present in the sample being tested. The color intensity produced is read, in accordance with the present embodiment, using a reader device, for example, a reflectance reader, adapted to read the test strip. The intensity of the color reflected by the colored label in the test region (or detection zone) of the test strip is directly proportional to the amount of analyte present in the sample being tested. In other words, a darker colored line in the test region indicates a greater amount of analyte, whereas a lighter colored line in the test region indicates a smaller amount of analyte. The color intensity produced, i.e., the darkness or lightness of the colored line, is read using a reader device, for example, a reflectance reader, adapted to read the test strip.

A reflectance measurement obtained by the reader device is correlated to the presence and/or quantity of analyte present in the sample. The reader takes a plurality of readings along the strip, and obtains data that are used to generate results that are an indication of the presence and/or quantity of analyte present in the sample. The system may correlate such data with the presence of a disorder, condition or risk thereof.

As mentioned above, in addition to reading the test strip, the reader may (optionally) be adapted to read a symbology, such as a bar code, which is present on the test strip or housing and encodes information relating to the test strip device and/or test result and/or patient, and/or reagent or other desired information. Typically the associated information is stored in a remote computer database, but can be manually stored. Furthermore, the symbology can be imprinted when the device is used and the information encoded therein.

SUMMARY

An immunoassay test strip is provided, wherein results of an immunoassay test of a patient sample are detectable by a change in color or other property of the test strip that can be detected using a reflectance reader. In one embodiment, the immunoassay test strip includes a sample pad for receiving a liquid patient sample; a conjugate pad fluidly coupled to the sample pad, wherein the conjugate pad contains a substantially uniform application of conjugate reagent; a contact pad fluidly coupled to the conjugate pad; a porous or bibulous member, e.g., made from nitrocellulose, fluidly coupled to the contact pad which is capable or transporting a liquid sample along the test strip, wherein the porous or bibulous member serves as the solid support upon which immunoreactions occur, and an absorbent pad fluidly coupled to the porous or bibulous member, which serves to draw sample fluid introduced onto the sample pad through the respective conjugate pad, contact pad and porous or bibulous member.

The porous or bibulous member may include an immobilized capture antibody that binds to an analyte of interest in the sample fluid in a detection zone. For example, the porous or bibulous member may have an antibody diffusively bound thereto. The results of the immunoassay test may be qualitative and/or quantitative. In one embodiment, the immunoassay test detects a presence of fetal fibronectin in the sample.

Other and further aspects and embodiments of the disclosed inventions will be apparent to those skilled in the art upon reviewing the following Detailed Description in conjunction with the accompanying figures.

BRIEF DESCRIPTION OF THE DRAWINGS

It will be appreciated that the system and apparatus shown in the drawings are not necessarily drawn to scale, with emphasis instead being placed on illustrating the various aspects and features of the illustrated embodiments, in which.

DETAILED DESCRIPTION

Reference is initially made to Prior Art FIGS. 1-5, which are taken from the above-incorporated U.S. Pat. No. 6,867,051.

Figure 1A:
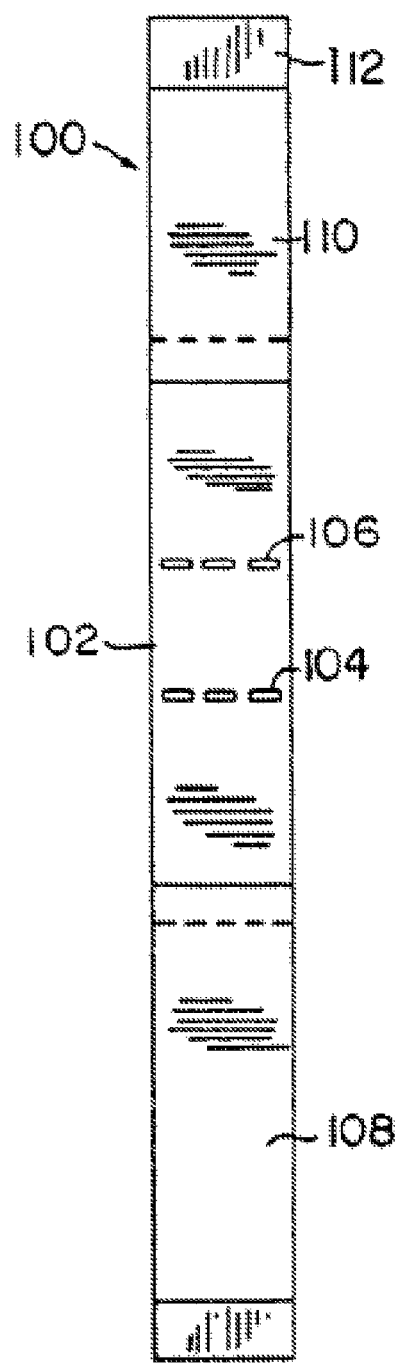
FIG. 1A is a top view of a prior art immunoassay test strip.
Figure 1B:
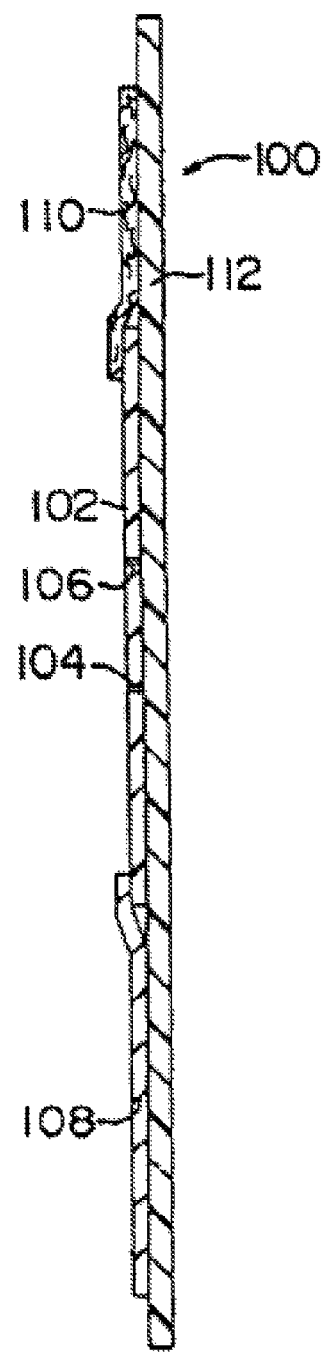
FIG. 1B is a side view of the immunoassay test strip of FIG. 1A.

As shown in FIGS. 1A and 1B, the prior art test strip 100 disclosed and described in the above-incorporated U.S. Pat. No. 6,867,051 includes a membrane system including three components: a porous or bibulous member 102; a conjugate pad 108; and an absorbent pad 110. The membrane system is mounted on a substrate or backing 112, with the conjugate pad 108 and the absorbent pad 110 slightly overlapping the porous or bibulous member 102, which is interposed therein between. As can be seen, the conjugate pad 108 overlaps the porous or bibulous member 102 so that a fluid sample placed onto the conjugate pad 108 is communicated from the conjugate pad 108 to the porous or bibulous member 102. Similarly, the absorbent pad 110 overlaps with the porous or bibulous member 102 so that fluid samples introduced into the porous or bibulous member 102 from the conjugate pad 108 are then be transmitted to the absorbent pad 110. In this manner, the respective conjugate pad 108, absorbent pad 110 and porous or bibulous member 102 are in fluid communication with one another, so that a fluid sample placed on the conjugate pad 108 is able to propagate through the conjugate pad 108 to the porous or bibulous member 102, and then from the porous or bibulous member 102 to the absorbent pad 110.

The porous or bibulous member 102 is capable of transporting a liquid sample along the test strip and serves as the solid support upon which the immunoreactions occur. Antibodies which react with the target analyte and/or label are immobilized on the solid support. Possible solid supports include paper and cellulose derivatives, such as cellulose esters and ethers, natural and synthetic polymeric materials, such as vinyl polymers and partially hydrolyzed derivatives, polycondensates, copolymers and inorganic materials. One such solid support is a nitrocellulose membrane. As can be seen in the figures, the porous or bibulous member 102 contains two distinct zones, a detection zone 104, and a control zone 106, at which two different antibodies are immobilized. The detection zone contains an immobilized capture antibody that binds the analyte of interest, whereas the control zone contains an immobilized antibody or other component, such as an antigen, that binds labeled antibody conjugate that has not bound to analyte. The conjugate pad 108 serves as a sample application component, and is striped with an antibody to the analyte, which is conjugated to a detectable label. In particular, the labeled antibody conjugate is diffusively bound to the conjugate pad 108 and becomes mobile upon application of the liquid sample and moves along the test strip 100. The conjugate pad 108 is made of a porous material, such as glass fiber. The conjugate pad 108 may also act as a pre-filter for the sample. The absorbent pad 110 serves to draw liquid continuously through the device, and may be made of a material such as cellulose paper or other material known to those of skill in the art.

Figure 2A:
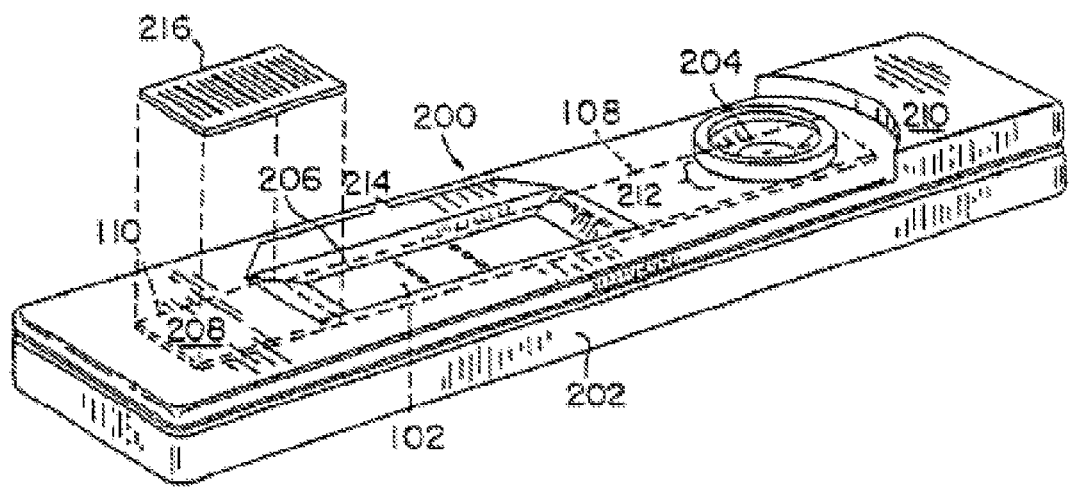
FIG. 2A is a perspective view of a prior art assay device, including the assay test strip of FIG. 1A and FIG. 1B and housing assembly and showing a bar code, which can optionally be affixed to the housing.

Referring now to FIG. 2A, the immunoassay device disclosed and described in the above-incorporated U.S. Pat. No. 6,867,051 includes a test strip (100) and housing assembly 200, wherein the housing 202 generally surrounds the test strip 100 (FIGS. 1A and 1B) and includes an opening through which test sample is applied 204, as well as an aperture above the detection and control zones 206 that permits measurement of the amount of label by the reader, which is correlated with the amount of analyte in the test sample. The housing 202 includes at its upper surface 208 a fattened end 210, used for gripping the housing 202, an application window 204 (or sample window) through which a sample is applied to a conjugate pad 108 of an immunoassay test strip within the housing 202. The housing 202 also includes a test window 214 through which the test result of the immunoassay is viewed. In accordance with the embodiments shown, no window material is mounted within the test window 214 (or the sample window 212). Thus, an optical path from outside the housing 202 through the test window 214 to the immunoassay test strip is unobscured by even a transparent material. Also, as shown in FIG. 2A and FIG. 2B, the housing may include a symbology, exemplified as a bar code 216 or 316 that can be read by the reader or a separate reading device and associated with identifying information pertaining to the particular device and/or test run or other information.

Figure 2B:
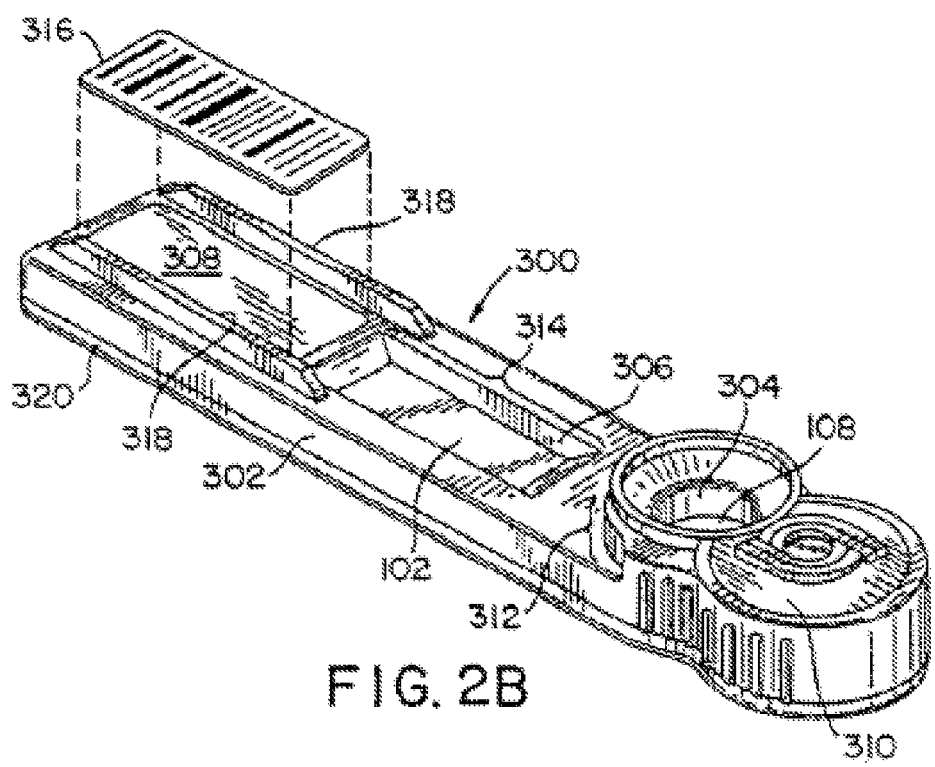
FIG. 2B is a perspective view of an alternative embodiment of a prior art assay device, including the assay test strip of FIG. 1A and FIG. 1B and housing assembly and showing a bar code, which can optionally be affixed to the housing.
Figure 3:
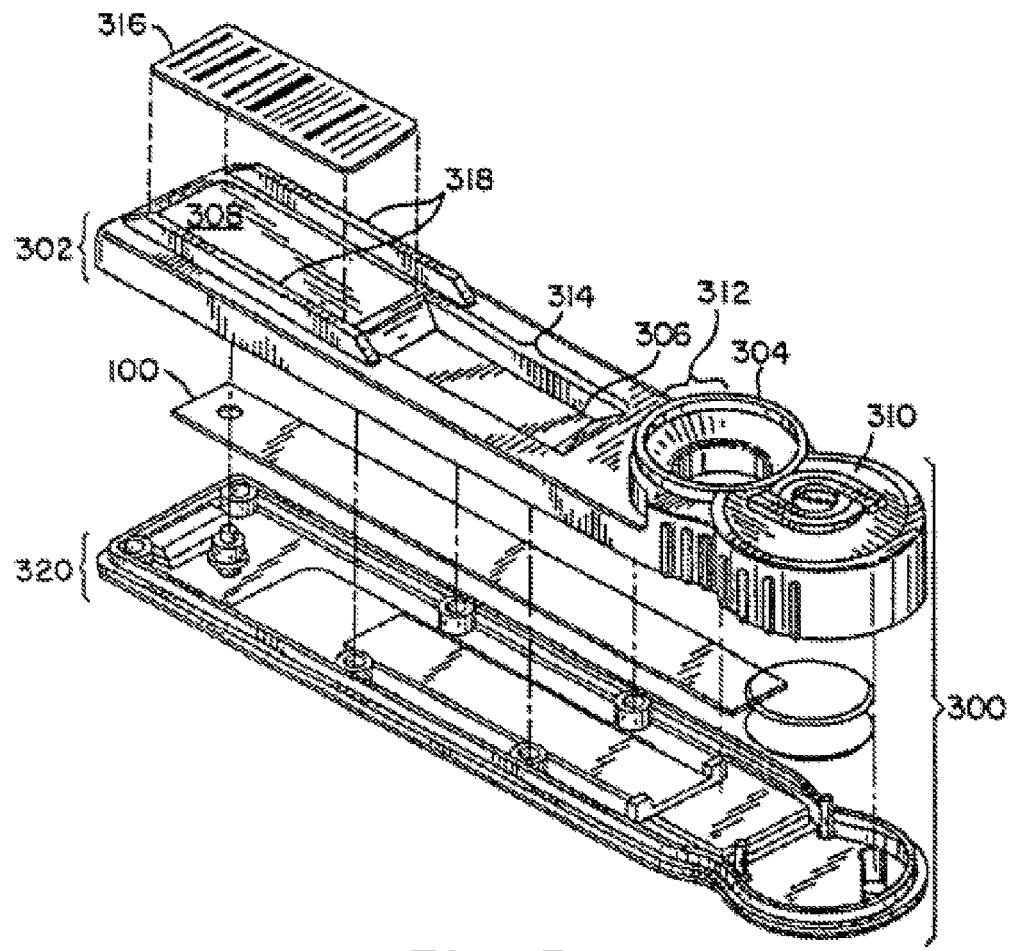
FIG. 3 is a perspective view of the assay device of FIG. 2B showing the individual components of the device.

An alternative embodiment of the test device is shown in FIG. 2B. The components of device are shown in FIG. 3 and include the upper and lower members 302 and 320 of the housing and the test strip 100. Also shown are the sample application port 304, test window 306, and the optionally included bar code 316.

Figure 4:
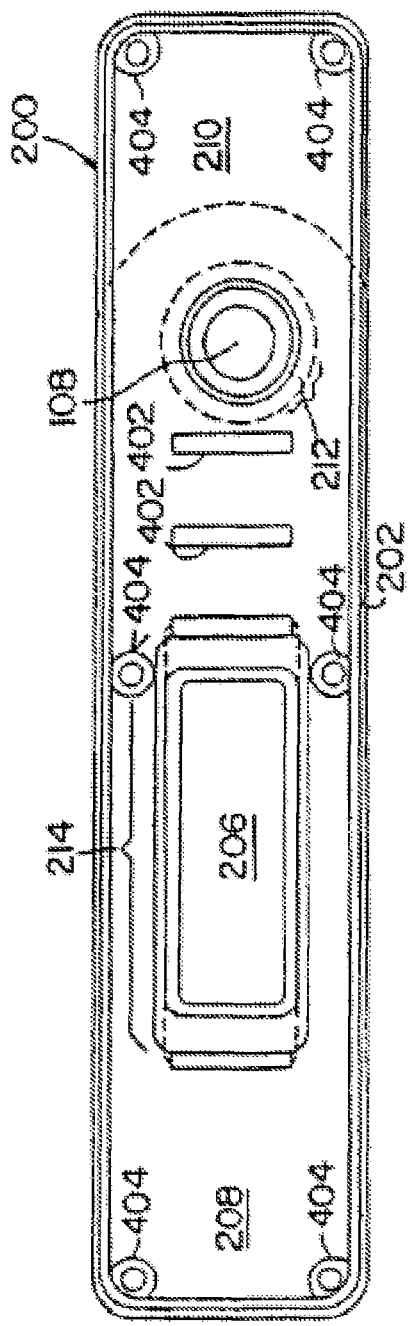
FIG. 4 is a top view of an exemplary prior art housing assembly for the assay test strip of FIGS. 1A and 1B.

FIG. 4 is a top view is shown of the immunoassay test strip housing 202 of FIG. 2A, showing the sample window 212, and the test window 214, and the enlarged gripping portion 210. Also shown are structures 402 for holding the immunoassay test assembly within the housing 202 and structures 404 for securing upper and lower halves of the housing 202 to one another.

Figure 5:
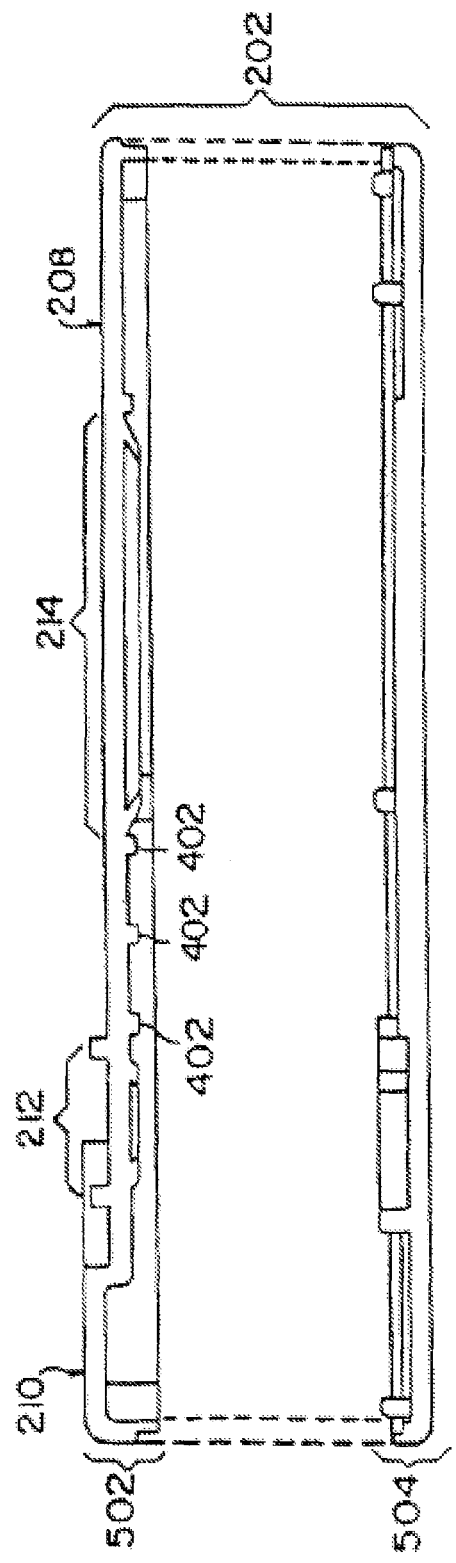
FIG. 5 is a side assembly view of the housing assembly of FIG. 4.

FIG. 5 is a side cross-sectional assembly view of the test strip housing 202, showing the sample window 212, the test window 214, and the structures 402 for holding the immunoassay test strip assembly in place within the housing 202. As can be seen, an upper half 502 of the housing 202 is mated with a lower half 504 of the housing 202. The immunoassay test strip is sandwiched between the upper and lower halves 502 and 504 of the housing 202 and is secured in place by the structures 402 of the upper half 502. The immunoassay test strip is positioned so as to be viewable through the test window 214 when the immunoassay test strip assembly is secured within the housing and the conjugate pad is positioned to be contactable through the sample window 212.

These above-described and illustrated devices of FIGS. 1-5 are particularly adapted for use with the reflectance reader disclosed and described in the above-incorporated U.S. Pat. No. 6,867,051.

Figure 6A:
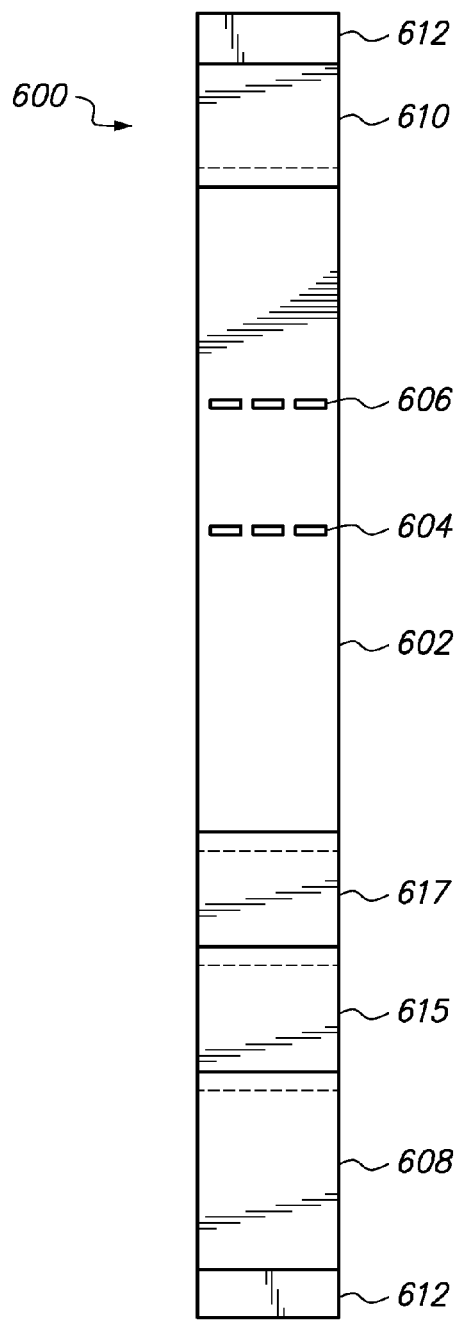
FIG. 6A is a top view of an improved immunoassay test strip constructed according to one embodiment of the disclosed inventions.
Figure 6B:
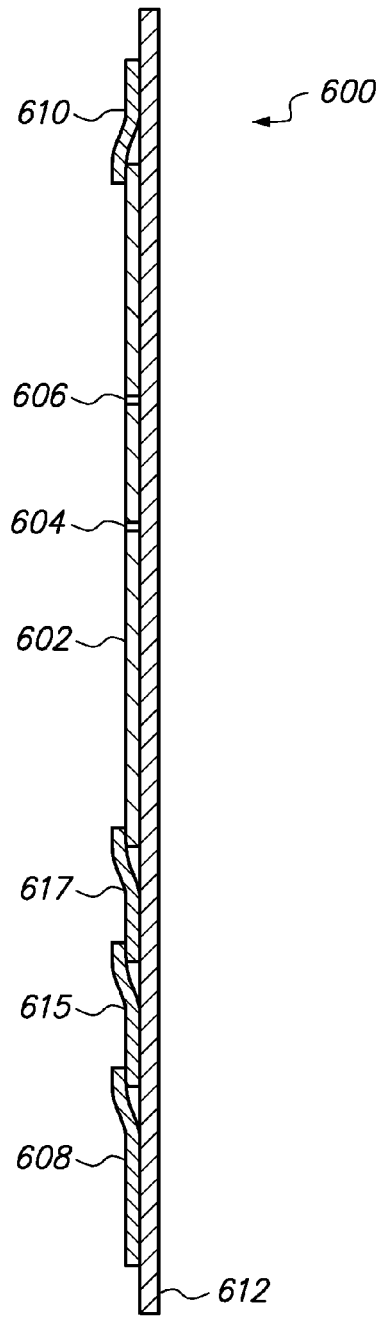
FIG. 6B is a side view of the immunoassay test strip of FIG. 6A.
Figure 7:
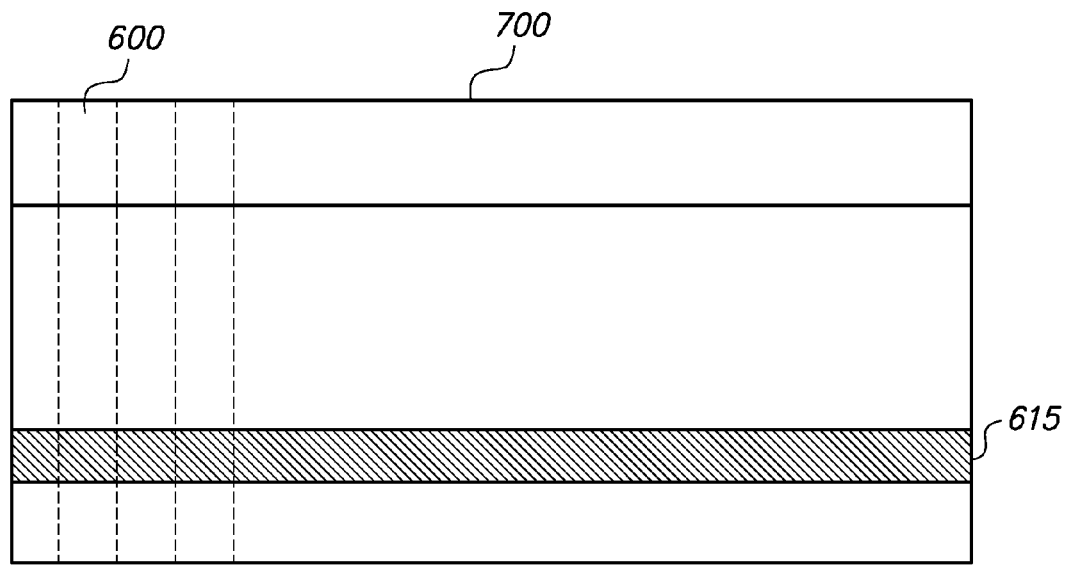
FIG. 7 is a picture of the top surface of a card from which test strips such as those shown in FIGS. 6A and 6B are cut, taken after the conjugate striping process has visually saturated the conjugate pad of the membrane system.
Figure 8:
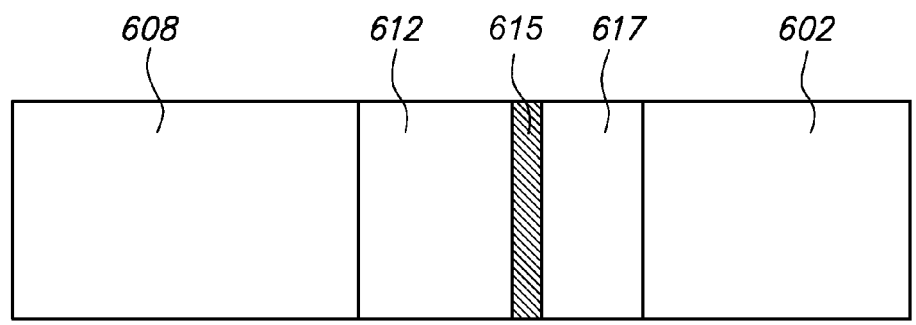
FIG. 8 is a picture of the top surface of a test strip similar to that shown in FIGS. 6A and 6B, taken with the conjugate pad removed to reveal an underlying portion of the contact pad, including conjugate material that is deposited in the contact pad from the conjugate pad during the striping process.

Embodiments of the inventions disclosed herein are illustrated in FIGS. 6-8, and are directed to an improved immunoassay test strip for use in a diagnostic system and related methods, and in particular for use in diagnostic systems and methods such as those disclosed and described in the above-incorporated U.S. Pat. No. 6,867,051. Specifically, exemplary embodiments of an improved immunoassay test strip disclosed and described herein are preferably sized and configured to be readily substituted for the prior art test strip 100 of FIGS. 1A and 1B, without requiring changes to the housing 200 or reader. However, it will be appreciated by those skilled in the art that the improved immunoassay test strips disclosed and described herein are not limited to use in the diagnostic systems and methods disclosed and described in the above-incorporated U.S. Pat. No. 6,867,051.

Referring now to FIGS. 6A and 6B, an exemplary embodiment of an improved immunoassay test strip 600 includes a membrane system having five main components: a sample pad 608; a conjugate pad 615; a contact pad 617; a porous or bibulous portion comprising a thin membrane of nitrocellulose 602; and an absorbent pad 610. The membrane system (608, 615, 617, 602, 610) of the test strip 600 is mounted on a suitable substrate or backing 612, wherein the sample pad 108 overlaps the conjugate pad 615, the conjugate pad 615 (slightly) overlaps the contact pad 617, and the respective contact pad 617 and absorbent pad 610 each overlap the nitrocellulose membrane 602, which is interposed therein between. In particular, and as can be seen in FIG. 6B, the sample pad 608 overlaps the conjugate pad 615 so that a fluid sample placed onto the sample pad 608, e.g., through an open sample window in a housing (not shown) that encases the immunoassay test strip 600 is readily communicated from the sample pad 608 to the conjugate pad 615. Similarly, the conjugate pad 615 slightly overlaps the contact pad 617, and the respective contact pad 617 and absorbent pad 610 overlap the nitrocellulose membrane 602, so that a fluid sample placed onto the sample pad 608 will readily propagate from the sample pad 608 to the conjugate pad 615, from the conjugate pad 615 to the contact pad 617, from the contact pad 617 into the nitrocellulose membrane 602, and from the nitrocellulose membrane 602 into the absorbent pad 610, respectively.

In this manner, the respective sample pad 608, conjugate pad 615, contact pad 617, nitrocellulose membrane 602 and absorbent pad 610 are all in fluid communication with one another. As explained in greater detail below, the materials used to form the respective membrane system components 602, 608, 610, 615 and 617, along with their respective dimensions and amount of respective overlap between adjacent components, will greatly influence the flow rate of sample fluid introduced onto the sample pad 608 all the way to the absorbent pad 610.

As with the porous or bibulous member 102 of the prior art test strip 100 of U.S. Pat. No. 6,867,051, the nitrocellulose membrane 602 of the present test strip 600 is capable of transporting a liquid sample, and also serves as the solid support upon which the immunoreactions occur. Antibodies which react with the target analyte and/or label are immobilized on the solid support. Possible solid supports include paper and cellulose derivatives, such as cellulose esters and ethers, natural and synthetic polymeric materials, such as vinyl polymers and partially hydrolyzed derivatives, polycondensates, copolymers and inorganic materials. As can be seen in FIGS. 6A and 6B, the nitrocellulose membrane 602 contains a distinct detection zone 604, and a distinct control zone 606, at which two different antibodies are immobilized. The detection zone 604 contains an immobilized capture antibody that binds the analyte of interest, whereas the control zone 606 contains an immobilized antibody or other component, such as an antigen, that binds labeled antibody conjugate that has not bound to analyte.

In order to better understand the improved immunoassay test strips, the individual components and an exemplary manufacturing process will now be described.

Sample Pad

The sample pad 608 of test strip 600 is essentially unchanged from the prior art test strip 100 of FIGS. 1A and 1B, except that it is not striped with any conjugate, and functions only as a sample fluid flow pathway.

Conjugate Pad

The conjugate pad 615 of test strip 600 has no counterpart component in the prior art test strip 100. In the illustrated embodiment, the conjugate pad is a pretreated hydrophilic material, such as Nylon, supplied by Porex Technologies. During the manufacturing process, after the respective nitrocellulose membrane 602 and (porous) contact pad 617 are applied (in the case of the nitrocellulose membrane 602) or adhered (in the case of the contact pad 617) to the substrate 612, the conjugate pad 615 is adhered to the substrate 612, so as to have one edge very slightly overlapping the contact pad 617 (as shown in FIG. 6B), with the other edge being very slightly separated from a temporary release liner covering over the adhesive substance on the substrate 612 to which the sample pad 608 will subsequently be adhered. Thereafter, but before the respective sample pad 608 and absorbent pad 610 are adhered to the substrate 612 (which remains in the form of an elongate card sized for making a large number, e.g., several dozen, test strips) is "striped" according to a well-known process, in which the respective antibodies and/or other components that form the detection zone 604 and the control zone 606 are applied to the nitrocellulose membrane 602, and the conjugate reagent material is simultaneously applied (deposited into) the conjugate pad 615.

In particular, the conjugate reagent is applied to the conjugate pad to the degree that the entire pad appears "visually saturated" (meaning that, while it may technically be able to hold additional volume, the reagent is evenly and completely distributed throughout the conjugate pad. Because the conjugate pad 615 has one edge slightly overlapping the contact pad 617 and another edge isolated from the release liner covering over the adhesive substance on the substrate 612 to which the sample pad 608 will subsequently be adhered, any "back end" wicking of any excess conjugate material will be prevented during the striping process, with any such excess conjugate material instead being absorbed by the contact pad 617. However, as seen in FIG. 8 (with the conjugate pad removed after the striping process), the contact pad 617 is sufficiently dense so that the excess conjugate does not wick into the nitrocellulose membrane 602. This arrangement is believed to provide a significant reduction in variability from test strip 600 to test strip 600 over the prior art test strips 100, because each resulting conjugate covered (substantially square) portion of the conjugate pad 615 holds a similar amount of conjugate. In addition, the conjugate comes off the conjugate pad 615 very consistently from test strip 600 to test strip 600.

In particular, it has been found that using a visually saturated pre-treated Porex material as the conjugate pad results in the sample mixing with the conjugated beads in-process, with the conjugate-sample mix coming off the conjugate pad 615 and moving into the into the contact pad 617 within seconds of application. In this manner, the conjugate pad 615 allows the test strip 600 to perform similar to a liquid immunoassay system having a strip run vertically (e.g., in a test tube), where a known amount of conjugate is added to and allowed to mix with the sample prior to adding to strip. The conjugate pads 615 are preferably square in their length-width dimensions once the test strip 600 is cut from the card.

In one embodiment, the conjugate pads 615 of the final test strip 600 are approximately 0.320" by 0.320" in their length-width dimensions.

Contact Pad

Like the conjugate pad 615, the contact pad 617 of test strip 600 also has no counterpart component in the prior art test strip 100. As described above, insertion of the additional contact pad 617 into the fluid path of the test strip 600 allows for using a striping process to apply the conjugate reagent to the conjugate pad 615 at the same time as the respective antibodies and/or other components that form the detection zone 604 and the control zone 606 are applied to the nitrocellulose membrane 602, because the contact pad 617 prevents any excess conjugate material from wicking from the conjugate pad 615 into the nitrocellulose material 602. Additionally, the contact pad 617 serves to gate the conjugate/sample mixture in-process, and meters it for a few minutes onto the nitrocellulose membrane 602. This in-process metering of the conjugate/sample mixture allows more binding and slows down the reaction, which in turn allows a more desired reaction time and sensitivity.

Absorbent Pad

The absorbent pad 610 of the test strip 600 is essentially unchanged from the prior art test strip 100 of FIGS. 1A and 1B, and functions to draw the sample fluid flow through the fluid pathway, and in particular through the nitrocellulose membrane 602.

Exemplary Manufacturing Process

In accordance with one embodiment, the lamination of the solid phase is carried out on a vinyl backing card (i.e., substrate 612) that is approximately 0.010"±0.0005" thick, 2.7" wide and 17.73" long, with release liners pre-scored at 10 mm, 18.25 mm, 23 mm and 56 mm. The 10 mm release liner will allow for a gap between the liner (which is covering the eventual location of the sample pad 608) and the conjugate pad 615. This gap is critical for striping the conjugate reagent without causing leakage on the back-end of the membrane 615.

The lamination sequence is as follows:
1. Nitrocellulose Membrane—Unisart (PN: 1UN95E) from Sartorius with 33 mm width. The nitrocellulose should have a thickness of 240-270 um (including 100 um polyester backing film) and wicking speed across the rolls of 90-135 s/4 cm (both based on manufacturers Certificate of Analysis).
2. Contact Pad—Whatman, Grade: S14, width: 5.8±0.1 mm, length approx. 450 mm.
3. Conjugate Pad—Porex [X-41210 (distributor #), X-4588 (Manufacturer #)] thin hydrophilic membrane, 0.025"±0.004" thick, pore size of 75-110 um. The pad is received in sheets of 10"×17.75" and cut into 0.0320" strips using the rotary cutter or it may also be pre-cut by Interstate Specialty Products into 17.75"×0.32" strips. It is important that Porex material not be received in rolls due to the memory capacity of the material and that it is stored in a dark environment.

Following the above first steps of the lamination process, the following reagent application on the solid phase is carried out using striping equipment:
4. Reagent Application—The A137-MS Conjugate reagent is striped at appropriate % solids, determined by titering the conjugate. Lot-to-lot variation in the Porex conjugate membrane and overlap variability between the conjugate pad and contact pad will influence the required conjugate reagent volume and needle position to ensure an appropriate saturation level.

FIG. 7 is a picture of the top surface of a card from which test strips such as those shown in FIGS. 6A and 6B are cut, taken after the conjugate striping process has visually saturated the conjugate pad of the membrane system. In particular, FIG. 8 depicts the conjugate pad 615 after it is completely covered with conjugate on both ends after conjugate application.

FIG. 8 is a picture of the top surface of a test strip similar to that shown in FIGS. 6A and 6B, taken with the conjugate pad removed to reveal an underlying portion of the contact pad, including conjugate material that is deposited in the contact pad from the conjugate pad during the striping process. In particular, FIG. 8 shows an example of a striped Rapid fFN 10Q strip with the (previously visually saturated) conjugate pad 615 removed. The area of the contact pad 617 where the respective conjugate pad 615 overlaps the contact pad 617 has a limited amount for conjugate material that had leaked "controllably" from the conjugate pad 615 onto the contact pad 617 during the striping process. This is representative of the ideal striped 10Q strip. In comparison, a contact pad that has "white" areas or areas missing some conjugate is less desirable and may contribute to higher variability. Both the complete coverage of the Porex and the controlled leakage onto the contact pad are necessary for acceptable striping.

After the reagent application onto the nitrocellulose membrane 602 and the conjugate pad 615, the cards are preferably left to dry overnight at controlled temperature. After drying, cards are preferably stored flat, desiccated in coolers.

After striping, the lamination of the solid phase continues, and includes placement of the sample pad 608 and the absorbent pad 610:
5. Sample Pad—Whatman, Grade: S14, width: 0.515"±0.005"
6. Absorbent Pad—Whatman Inc, width: 0.65" with 684-753 um thickness and 13.9-16.2 s/300 ml/sq" porosity, grade: C7218

The cards are preferably rolled after final lamination (either at lamination step or at cutting step).

It will be appreciated by the skilled in the art that the disclosed inventions may be embodied in other specific forms besides and beyond those illustrated in FIGS. 6-8 and described herein. The foregoing embodiments are therefore to be considered in all respects illustrative rather than limiting.

What is claimed is:

1. A method of manufacturing an immunoassay test strip, wherein results of an immunoassay test of a patient sample are detectable by a change in color or other property of the resulting immunoassay test strip using a reflectance reader, the method comprising:
    applying a porous or bibulous member to a substrate, wherein the porous or bibulous member is capable of transporting a liquid sample and serves as a solid support upon which immunoreactions may occur;
    adhering a contact pad to the substrate adjacent a first end of the porous or bibulous member, with an edge of the contact pad overlaying, so as to be fluidly coupled with, the porous or bibulous member;
    adhering a conjugate pad to the substrate adjacent the contact pad, with an edge of the conjugate pad overlaying, so as to be fluidly coupled with, the contact pad;
    applying a conjugate reagent to the conjugate pad through a striping process, so that the conjugate pad thereafter contains a substantially uniform application of conjugate reagent;
    attaching a sample pad to the substrate adjacent the conjugate pad, with an edge of the sample pad overlaying, so as to be fluidly coupled with, the conjugate pad, the sample pad comprising material suitable for receiving a liquid patient sample; and attaching an absorbent pad to the substrate adjacent a second end of the porous or bibulous member opposite the first end, with an edge of the absorbent pad overlaying, so as to be fluidly coupled with, the porous or bibulous member, wherein the absorbent pad serves to draw sample fluid introduced onto the sample pad through the respective conjugate pad, contact pad, and porous or bibulous member, wherein the presence of the contact pad during the striping process prevents excess liquid conjugate reagent from wicking from the conjugate pad into the porous or bibulous material, while still allowing for a combination of patient sample liquid and conjugate reagent to flow from the conjugate pad, through the contact pad, into the porous or bibulous material during a subsequent immunoassay test.

2. The method of claim 1, wherein the conjugate pad comprises a pretreated hydrophilic material.

3. The method of claim 1, wherein the conjugate reagent applied during the striping process is allowed to dry prior to attaching the sample pad.

4. The method of claim 1, wherein the porous or bibulous member comprises nitrocellulose.

5. The method of claim 1, further comprising applying an immobilized binding partner of an analyte of interest in a sample fluid to the porous or bibulous member.

6. The method of claim 5, wherein the immobilized binding partner comprises a capture antibody that binds to the analyte of interest.

7. The method of claim 1, wherein the conjugate pad is adhered to the substrate such that the contact pad is longitudinally between the conjugate pad and the porous or bibulous member.

8. The method of claim 1, wherein the sample pad is attached to the substrate comprises such that the conjugate pad is longitudinally between the sample pad and the contact pad.

* * * * *